United States Patent [19]

Knorr et al.

[11] Patent Number: 5,153,345

[45] Date of Patent: Oct. 6, 1992

[54] PROCESS FOR THE PREPARATION OF ALKYL METHYL-3-CARBALKOXYETHYLPHOSPHINATES

[75] Inventors: Harald Knorr, Frankfurt am Main; Hilmar Mildenberger, Kelkheim(Taunus); Hans J. Nestler, Königstein, all of Fed. Rep. of Germany

[73] Assignee: Hoechst Aktiengesellschaft, Frankfurt am Main, Fed. Rep. of Germany

[21] Appl. No.: 599,662

[22] Filed: Oct. 18, 1990

[30] Foreign Application Priority Data

Oct. 20, 1989 [DE] Fed. Rep. of Germany ....... 3934916

[51] Int. Cl.$^5$ .............................................. C07F 9/40
[52] U.S. Cl. .................................. 558/98; 558/179
[58] Field of Search ........................................... 558/98

[56] References Cited

U.S. PATENT DOCUMENTS 4,062,888 12/1977 Ohorodnik et al. ................. 562/876
4,399,287 8/1983 Baillie et al. ........................ 548/119

FOREIGN PATENT DOCUMENTS

0030424B1 6/1981 European Pat. Off. .
2531238 10/1976 Fed. Rep. of Germany .

OTHER PUBLICATIONS

Houben-Weyl, Methoden der Organischen Chemie, Bd. XII/1, p. 248 (1963).
Khairullin, et al., *Reaction of Methyldichlorophosphine with Acrylic Acid*, Translated from Zhurnal Obshchei Khimii, vol. 37, No. 3, pp. 710-714 (1967).
Khairullin, et al., *Synthesis and Some Properties of Ethyl 3-(chloroethylphosphinyl) propionate*, Translated from Zhurnal Obshchei Khimii, vol. 39, No. 2, pp. 341-346 (1969).
Khairullin, V. K., *Reaction of Ethyldichlorophosphine with α, β-unsaturated acids*, Translated from Doklady Akademii Nauk SSSR, vol. 162, No. 4, pp. 827-828 (1965).
Khairullin, et al., *Reaction of Ethylphosphonous Dichloride with Crotonic Acid*, Translated from Zhurnal Obshchei Khimii, vol. 36, No. 3, pp. 494-498 (1966).
March, J. Advanced Organic Chemistry, Third Edition, J. Wiley and Sons, 1985, pp. 346-347.
Wagner et al. "Synthetic Organic Chemistry", (1953) pp. 481-482.

Primary Examiner—Mary C. Lee
Assistant Examiner—Michael G. Ambrose
Attorney, Agent, or Firm—Curtis, Morris & Safford

[57] ABSTRACT

Process for the preparation of compounds of the formula

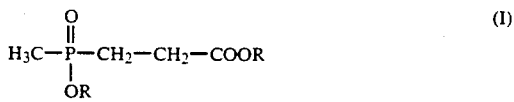
(I)

where R is $(C_1-C_4)$alkyl, which comprises reacting a compound of the formula II

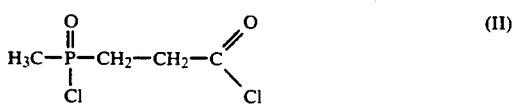
(II)

with an alcoholate of the formula III

Met-OR (III)

where Met is Na or K and R has the abovementioned meaning, at temperature from −30° C. to +10° C.

11 Claims, No Drawings

PROCESS FOR THE PREPARATION OF ALKYL METHYL-3-CARBALKOXYETHYLPHOSPHI-NATES

The present invention relates to a process for the preparation of compounds of the formula I

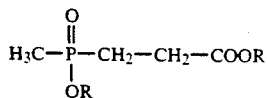

where R is $(C_1-C_4)$alkyl, which comprises reacting a compound of the formula II

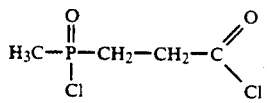

with an alcoholate of the formula III

where Met is Na or K and R has the abovementioned meaning, at temperatures from $-30°$ C. to $+10°$ C.

R is preferably methyl and ethyl.

A temperature range from $-20°$ C. to $0°$ C. is preferred.

$R=(C_1-C_4)$ alkyl is methyl, ethyl, n-propyl, iso-propyl, n-butyl, sec.-butyl or tert.-butyl.

The compounds of the formula I are important precursors and intermediates in the synthesis of herbicidally active substances (EP-A 30,424).

It is known to react structurally simple phosphonic acid halides with alcoholates to give the corresponding phoshphinic esters. However, the yields in these processes are unsatisfactory (<50%; Houben-Weyl, Methoden der org. Chemie [Methods in Organic Chemistry], Vol. XII/1 (1963) p. 248), in particular when the use of inert solvents is dispensed with. It is possible to achieve product yields of about 80% by adding the solvent benzene.

The preparation of phosphinic esters I in accordance with other references in the literature also gives yields which must be considered as insufficient on an industrial scale. For example, only 32 to 41% of product yield are obtained following Chairullin, Sobchuk, Pudovik, Z. obsc. Chim. 37 (1967) No. 3, page 710–714, engl. p. 660–669. Using benzene as a solvent, only 47% of theory of the desired ester are obtained with cold ethanol (Chairullin, Vasjanina, Pudovik, Z. obsc. Chim. 39 (1969) No. 2, page 341–346).

According to Chairullin (Doklady Akad. Nauk SSSR 162 (1965) No. 4, page 827–828), the compounds of the formula I are obtained in 50–58% yield if triethylamine is present as an auxiliary base. In the distillation of the crude reaction product, high-boiling anhydrides are formed (Z. obsc. Chim. 36 (1966) No. 3, page 494–498).

Thus, the alkyl phosphinates I obtained by the process known from the literature must be subjected to additional purification operations before they are further used in subsequent reactions. Moreover, the by-products which are obtained in substantial yields must be worked up and/or disposed of, which is to be considered disadvantageous from the economical and ecological point of view.

All these shortcomings mentioned are avoided in the process according to the invention, in which the desired products I are obtained in yields of $\geq 95\%$ of theory and in such a high purity that they can be used immediately for subsequent reactions. Moreover, the process according to the invention is very simple to operate and is also suitable for continuous operation.

Examples of the alcoholates III to be used according to the invention which may be mentioned are sodium isopropylate, potassium tert.-butylate, sodium butylate, but in particular sodium methylate and sodium ethylate.

The compound of the formula II is accessible from methyldichlorophosphane and acrylic acid (Chairullin, Sobcuk, Pudovik, Z.obsc.Chim. 37 (1967) No. 3, page 710–714). The preparation of the alcoholates III (or of the corresponding alcoholate solutions) is known to any person skilled in the art.

The compounds II and III are reacted in a temperature range from $-30°$ C. to $+10°$ C., but preferably between $-20°$ C. and $0°$ C.

The quantity of alcoholate required for the preparation of the compound of the formula I is at least 2 moles per mole of educt II. Naturally, the quantity of alcoholate must be increased if the educt of the formula II employed is contaminated by "acidic" secondary components, such as, for example, 2-methyl-5-oxo-1,2-oxaphospholane 2-oxide (German Offenlegungsschrift 2,531,238), which components, in turn, can react with the alcoholate III.

The alcoholates are employed in the form of an alcoholic solution. It is expedient to add additional quantities of the corresponding alcohol to the reaction mixture. This alcohol acts as the diluent so that the reaction mixture can still be stirred at the low reaction temperatures according to the invention. However, additional inert solvents such as, for example, benzene, are not required (see Examples 1–3).

The process according to the invention can be carried out expediently in such a manner that the alcoholate solution is initially introduced at $-20°$ C. to $0°$ C., and the dichloride II is metered in at this temperature. The stirred reaction mixture is allowed to come to room temperature, precipitated salt is filtered off, and the low-boiling compounds are distilled off. The crude product which remains is then purified in a high vacuum by short-path distillation. In this process, the esters of the formula I are obtained in purities of more than 97% (GC).

The following examples are intended to further illustrate the invention:

EXAMPLE 1

Methyl methyl-3-carbomethoxyethylphosphinate I 339 g (1.883 mol) of sodium methylate solution (30 % strength in methanol) and 200 ml of methanol are initially introduced at $-20°$ C., and 189 g of methyl-3-chlorocarbonylethylphosphinyl chloride (88.4% pure) are metered in in the course of 45 minutes. Stirring is continued for 30 minutes at $-20°$ C., and the reaction mixture is then allowed to come to room temperature. The sodium chloride (96.5 g) is filtered off with suction and washed with a little methanol, and the mother liquor is concentrated. 191.3 g of crude product are then obtained, from which another 7.8 g of sodium chloride precipitate. The mixture which is obtained after refiltration has the following composition (GC): 85.6% of product I (98.7% of theory), 14.0% of Na salt of methyl-3-carbomethoxyethylphosphinate, which is attributable to the 2-methyl-5-oxo-1,2-oxaphospholane 2-oxide, contained in the dichloride II as an impurity. Distillation over a short-path evaporator at 0.25 mbar (jacket temperature 130° C.) gives 159.8 g of product of the formula I which, according to GC, is 97% pure. This corresponds to a product yield of 97.4% of theory. The reaction product also contains 2.5% of methyl-3-carbomethoxyethylphosphinic acid.

EXAMPLE 2

Methyl methyl-3-carbomethoxyethylphosphinate I 353 g of 30% strength sodium methylate solution (1.96 mol) and 200 ml of methanol are initially introduced at −10° C., and 189 g of methyl-3-chlorocarbonylethylphosphinyl chloride (96.0% pure) are metered in the course of 45 minutes. Stirring is briefly continued at −10° C., and the mixture is then allowed to come to room temperature. The sodium chloride is filtered off with suction and washed with a little methanol and the mother liquor is concentrated. After sodium chloride has again been filtered off, 180.9 g of crude product are obtained which, according to GC, has the following composition: 93.6% of product I (98.0% of theory), 4.5% of the Na salt of methyl-3-carbomethoxyethylphosphinic acid. This product can be used undistilled for the subsequent reaction in accordance with EP-A 30,424. However, most of the amount of monoester can be separated off by distillation as described under Example 1.

EXAMPLE 3

Ethyl methyl-3-carbethoxyethylphosphinate I

Sodium ethylate (1.82 mol) is formed from 700 ml of absolute ethanol and 42.1 g of Na. The substance is cooled to −20° C., and 189 g of methyl-3-chlorocarbonylethylphosphinyl chloride (84% pure) are added at this temperature in the course of 45 minutes. The mixture is then allowed to come to room temperature and stirring is continued for 1 hours. The sodium chloride is filtered off with suction, and the low-boiling compounds are distilled off. What remains is a residue of 193.2 g which contains 85.9% (95% of theory) of ethyl methyl-3-carbethoxyethylphosphinate besides 9.3% (11.9% of theory) of methyl-3-carbethoxyethylphosphinic acid and 4.8% (6.1% of theory) of ethyl methyl-3-carboxyethylphosphinate. Distillation over a short-path evaporator at 0.3 mbar (jacket temperature 140° C.) gives 168.5 g of product I, which, according to GC (silylated), is 98.3% pure. This corresponds to a product yield of 94.8% of theory.

EXAMPLE 4

Comparison Example

Methyl methyl-3-carbomethoxyethylphosphinate I 2.2 moles of methanol are initially introduced while refluxing. 189 g (84% pure) of methyl-3-chlorocarbonylethylphosphinyl chloride are added in the course of 1 hour. A vigorous evolution of waste gas, takes place. Stirring is continued for 30 minutes. The low-boiling components are then distilled off. This gives 172.3 g of crude product which, according to GC, consist of 98.6% methyl-3-carbomethoxyethylphosphinic acid.

EXAMPLE 5

Comparison Example 200 ml of methanol and 2.0 moles of triethylamine are initially introduced at 0° C. 189 g (84% pure) of methyl-3-chlorocarbonylethylphosphinyl chloride of the formula II are added in the course of 1 hour, during which process the temperature should remain the same. A precipitate of triethylamine hydrochloride is formed. The mixture is concentrated, the salt is filtered off, and a crude product which, besides 38% of theory of methyl-3-carbomethoxyethylphosphinic acid, contains about 52% of methyl methyl-3-carbomethoxyethylphosphinate. Further P-containing components are additionally present in the reaction mixture.

We claim:

1. A process for the preparation of compounds of the formula I

where R is (C$_1$–C$_4$) alkyl, which comprises reacting a compound of the formula II

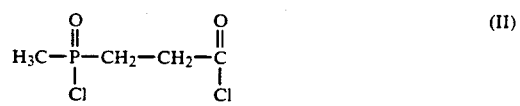

with at least 2 moles per mole of the formula II compound of an alcoholate of the formula III

where Met is Na or K and R has the above-mentioned meaning and wherein the alcoholate of formula III is employed in the form of a solution in the respective alcohol and without addition inert solvent at temperatures from −30° C. to +10° C.

2. The process as claimed in claim 1, wherein the reaction temperature is −20° C. to 0° C.

3. The process as claimed in claim 1, wherein R is methyl.

4. A process as claimed in claim 1, wherein 2 to 2.2 moles, per mole of the formula II compound, of the alcoholate of the formula III are employed.

5. A process as claimed in claim 1, wherein R is ethyl.

6. A process as claimed in claim 2, wherein R is methyl.

7. A process as claimed in claim 4, wherein R is methyl.

8. A process as claimed in claim 2, wherein R is ethyl.

9. A process as claimed in claim 4, wherein R is ethyl.

10. A process as claimed in claim 9, wherein the reaction temperature is −20° C. to 0° C.

11. A process as claimed in claim 7, wherein the reaction temperature is −20° C. to 0° C.

* * * * *